United States Patent [19]

Durman

[11] Patent Number: 5,330,437
[45] Date of Patent: Jul. 19, 1994

[54] SELF SEALING FLEXIBLE ELASTOMERIC VALVE AND TROCAR ASSEMBLY FOR INCORPORATING SAME

[75] Inventor: Bernard J. Durman, Loveland, Ohio

[73] Assignee: Ethicon Endo-Surgery, Cincinnati, Ohio

[21] Appl. No.: 152,758

[22] Filed: Nov. 12, 1993

[51] Int. Cl.⁵ ............................................. A61M 5/00
[52] U.S. Cl. ................................. 604/167; 137/846; 251/149.1
[58] Field of Search ................. 604/167, 169, 256; 137/846; 251/149.1

[56] References Cited

U.S. PATENT DOCUMENTS

| | | | |
|---|---|---|---|
| 3,118,468 | 1/1964 | Bochan | 137/846 |
| 3,861,416 | 1/1975 | Wichterle | 137/525.3 |
| 4,143,853 | 3/1979 | Abramson | 251/149.1 |
| 4,177,814 | 12/1979 | Knepshield et al. | 128/348 |
| 4,222,126 | 9/1980 | Boretos et al. | 3/1.5 |
| 4,364,127 | 12/1982 | Pierce et al. | 3/1.5 |
| 4,424,833 | 1/1984 | Spector et al. | 137/849 |
| 4,475,548 | 10/1984 | Muto | 128/207.14 |
| 4,524,805 | 6/1985 | Hoffman | 137/846 |
| 4,673,393 | 6/1987 | Suzuki et al. | 604/167 |
| 4,798,594 | 1/1989 | Hillstead | 604/167 |
| 4,809,679 | 3/1989 | Shimonaka et al. | 128/4 |
| 4,960,412 | 10/1990 | Fink | 604/256 |
| 5,092,857 | 3/1992 | Fleischhacker | 604/167 |
| 5,104,383 | 4/1992 | Shickman | 604/167 |
| 5,141,498 | 8/1992 | Christian | 604/167 |
| 5,224,952 | 7/1993 | Deniega et al. | 606/184 |
| 5,242,412 | 9/1993 | Blake | 604/167 |
| 5,269,763 | 12/1993 | Boehmer et al. | 604/167 |

FOREIGN PATENT DOCUMENTS 621928  12/1992  Belgium ............................... 137/846

*Primary Examiner*—Paul J. Hirsch
*Attorney, Agent, or Firm*—Matthew S. Goodwin

[57] ABSTRACT

A self sealing flexible elastomeric valve is disclosed. The valve can be used to seal a trocar device from loss of gas pressure during a laparoscopic surgical procedure when a surgical instrument is inserted therethrough as well as when no instrument is inserted. The preferred one piece valve includes a flange having an aperture, and a cylindrical wall section which extends to a pair of mutually opposed sealing wall sections defining a generally S-shaped slit. This slit configuration at the end of these wall sections define the sealing surfaces. The flange preferably includes a concentrically dome shaped region with the aperture centrally displayed. The valve also is preferably composed of a silicone rubber. The valve has the advantages of simplicity of manufacture and assembly and the ability to provide an adequate seal against the surface of any surgical instrument inserted through it. Also, the improved valve will require a small amount of force to insert instruments and will resist eversion of the valve walls when instruments are withdrawn. A trocar assembly incorporating the sealing valve as described above is also disclosed.

13 Claims, 7 Drawing Sheets

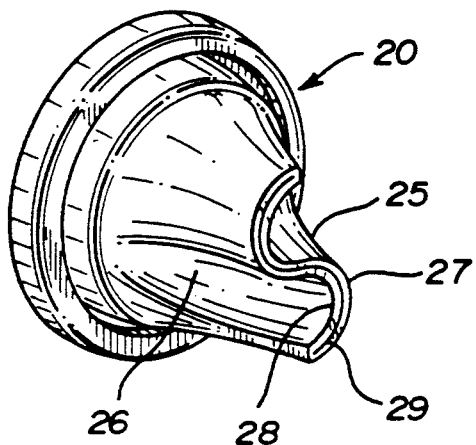
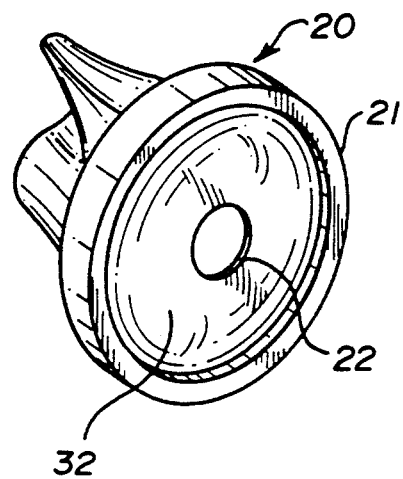
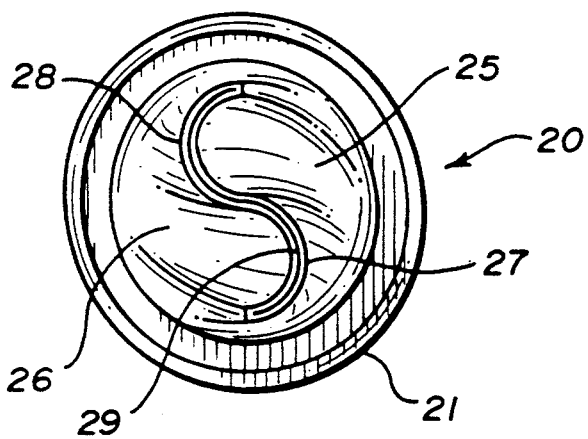
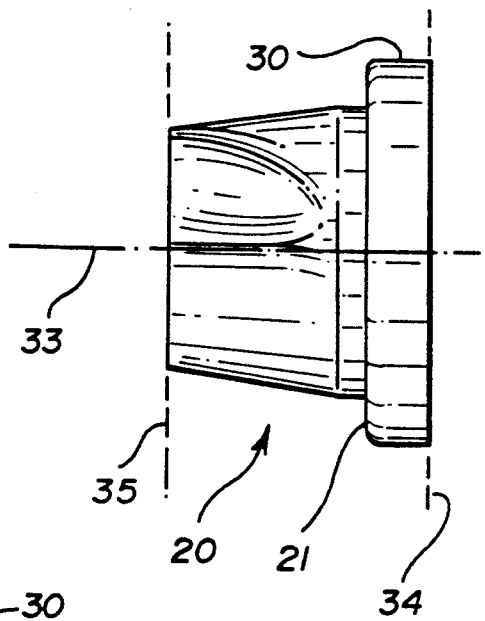
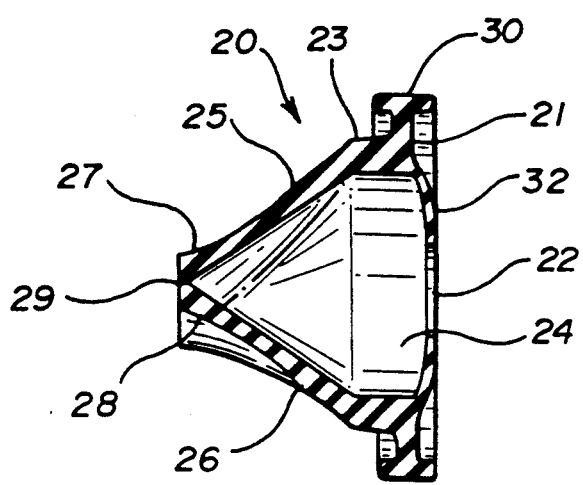

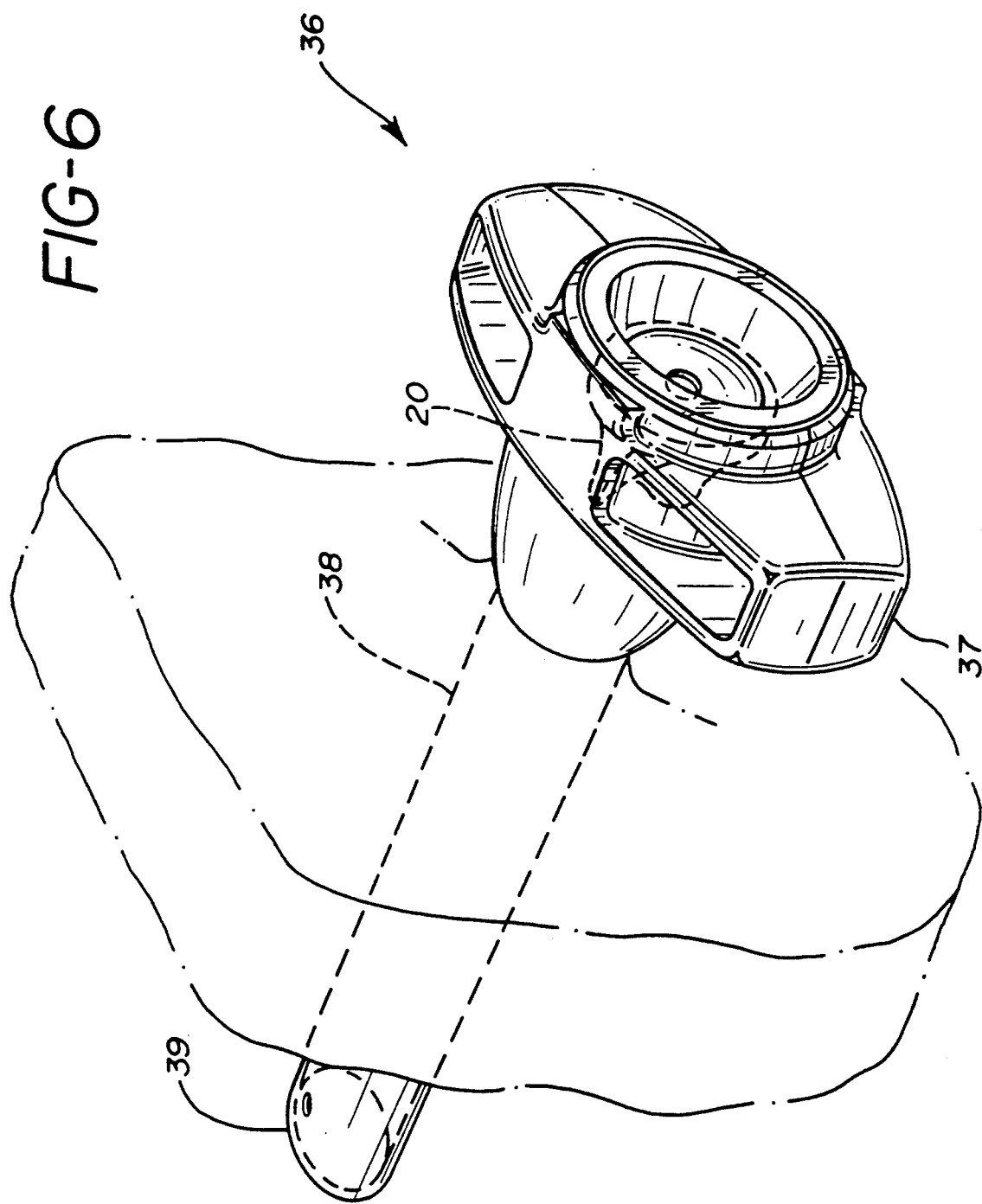

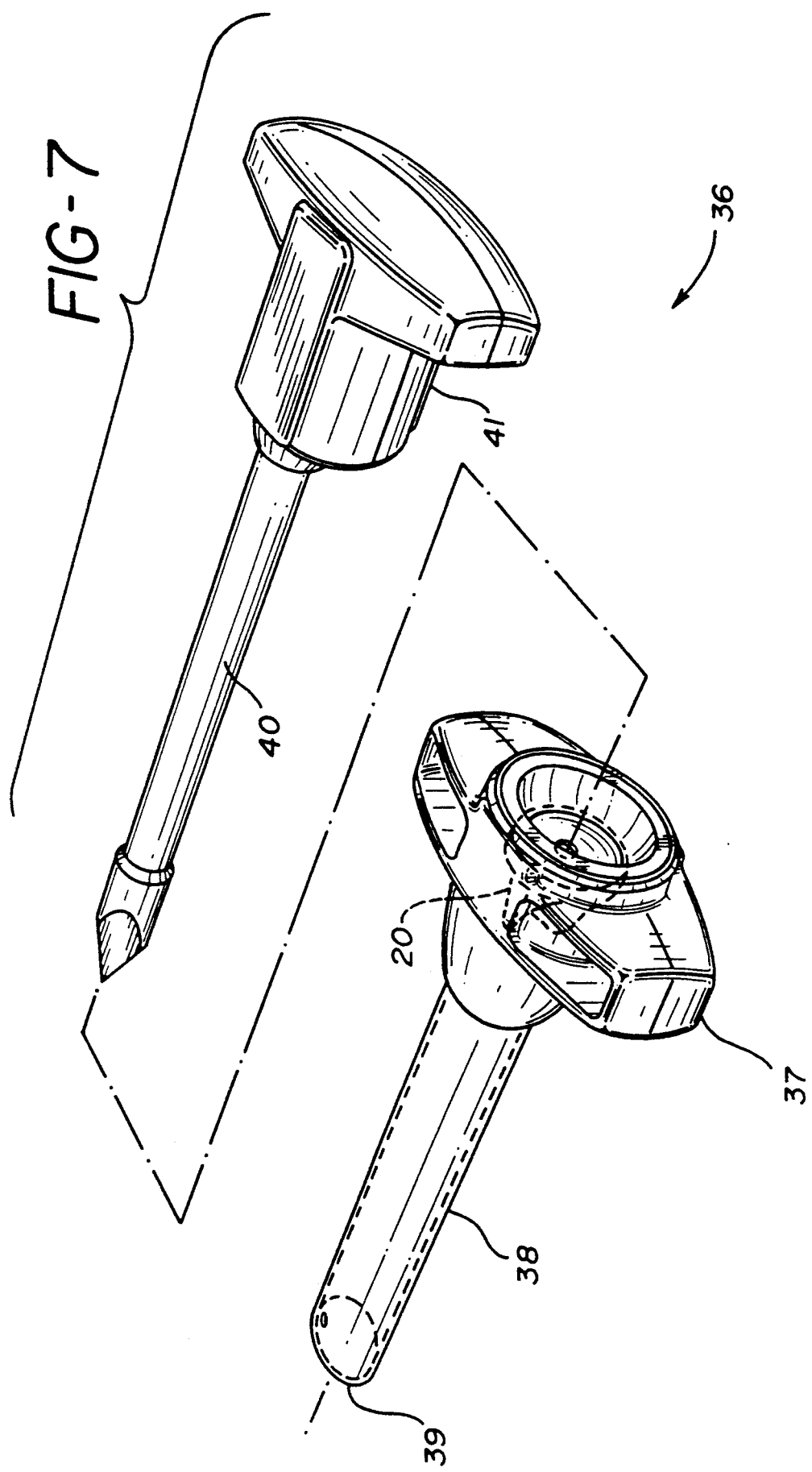

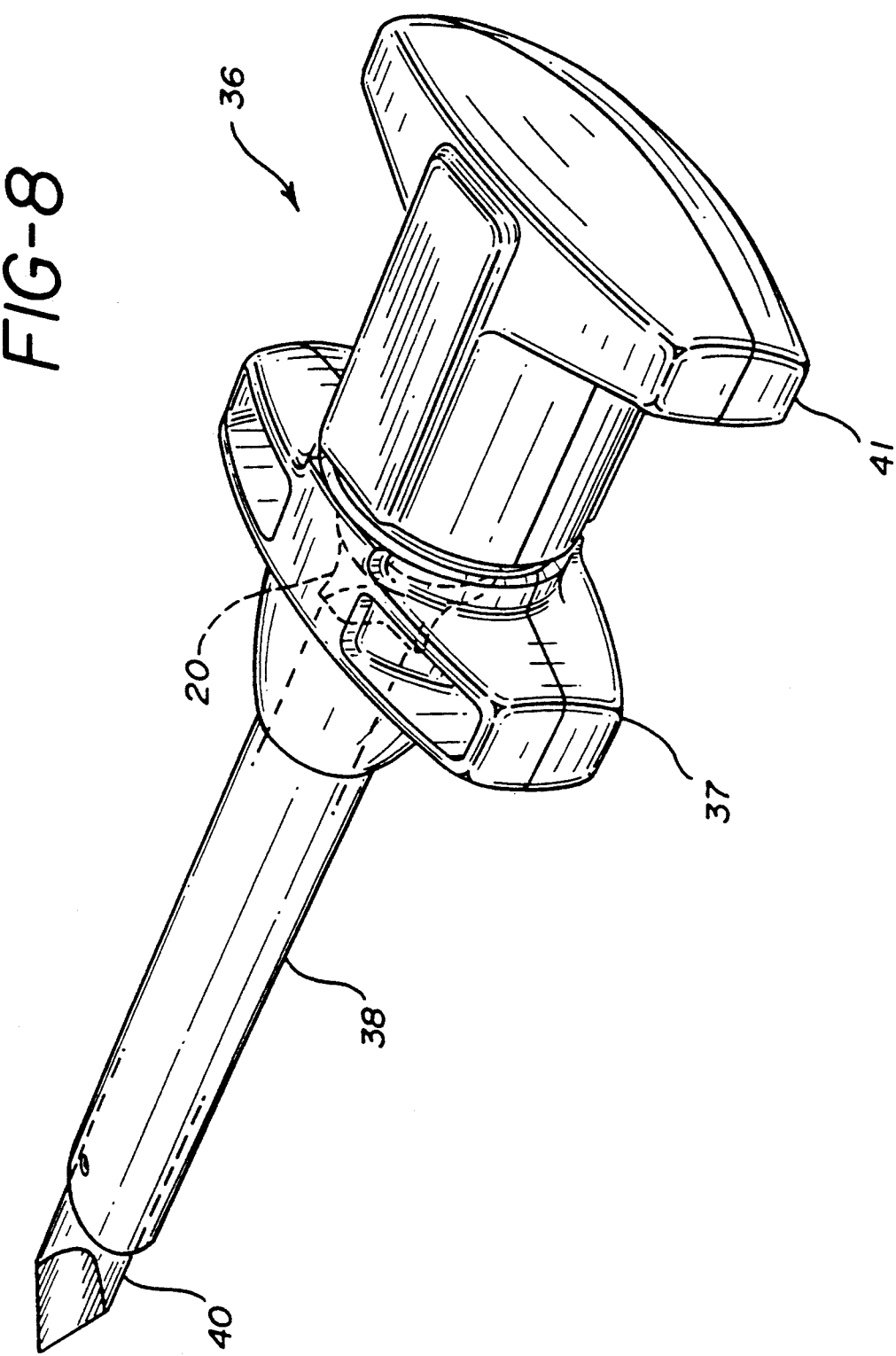

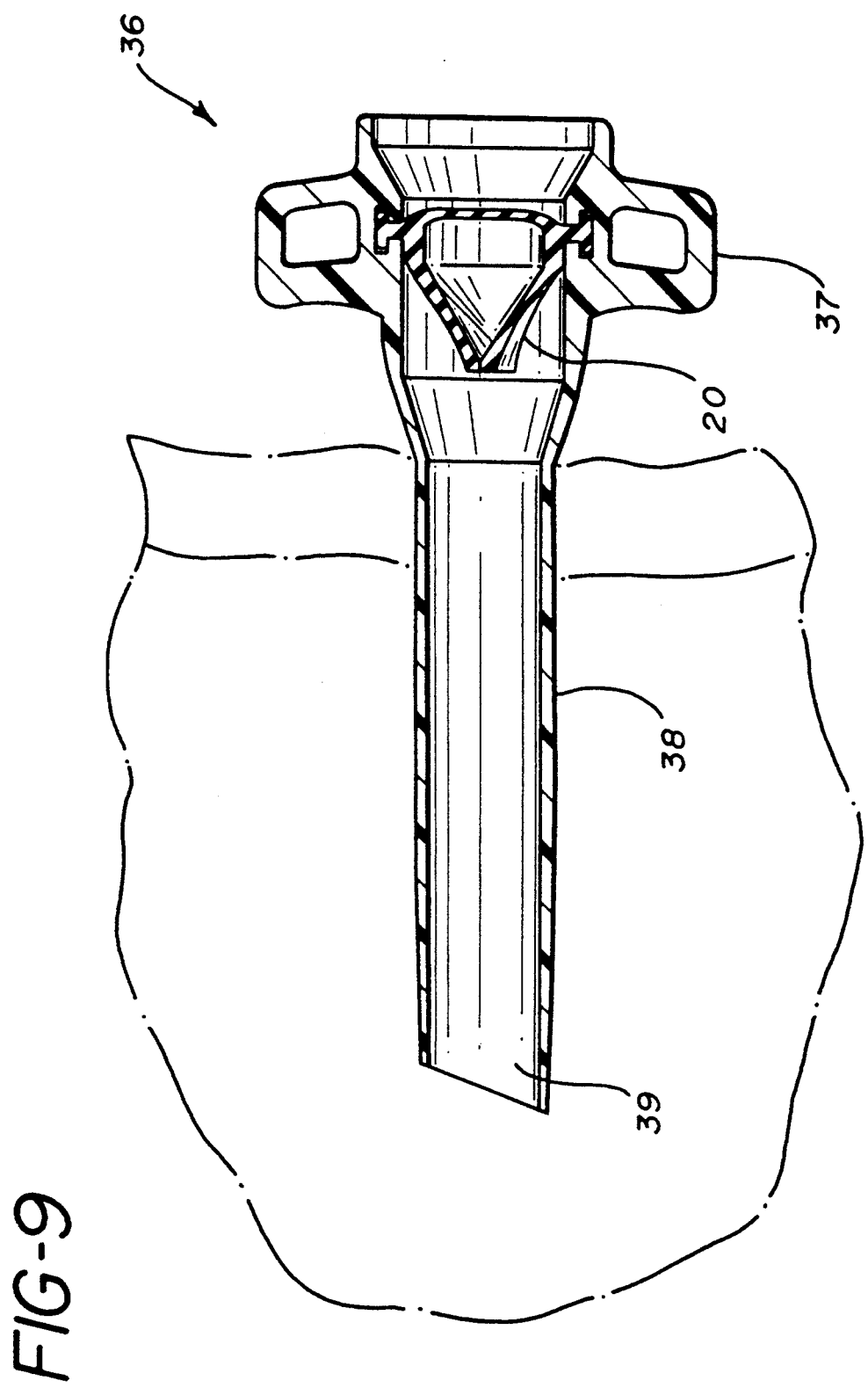

SELF SEALING FLEXIBLE ELASTOMERIC VALVE AND TROCAR ASSEMBLY FOR INCORPORATING SAME

BACKGROUND OF THE INVENTION

This invention relates generally to a self sealing valve which provides and maintains a seal when an instrument or device is inserted through, or withdrawn from, the valve. More specifically, it relates to a flexible, elastomeric self sealing valve especially well suited for use with surgical instruments, such as trocar assemblies necessary for numerous laparoscopic surgical procedures.

Sealing devices for trocar assemblies are an important aspect of the design of instruments used in laparoscopic surgical procedures. A laparoscopic surgical procedure utilizes several small puncture openings, mainly in the abdominal wall, to allow insertion of specialized surgical instruments instead of one large incision in a traditional open surgical procedure. The laparoscopic procedure is becoming widely accepted because of its many advantages such as: less trauma to the patient, shorter recovery time, reduced adhesions, and post operative pain. The laparoscopic surgical technique requires inflation of the abdominal cavity to lift the abdominal wall from the internal organs to create working space for the surgeon and to introduce light generating and optical viewing instruments.

During the laparoscopic surgical procedure, the internal gas pressure must be maintained in order to successfully complete the procedure. In order to maintain the internal gas pressure while instruments are passed into and out of the openings in the abdominal cavity, sealing devices are required for both the instruments and for the trocar assemblies used to make and maintain the small openings. It is desirable for such sealing devices to seal any opening within the trocar assembly when the obturator, which is the puncturing component of the trocar assembly, is withdrawn after puncturing the abdominal wall. It is also desirable to seal when other surgical instruments are inserted through the trocar cannula, which is the hollow tube of the trocar assembly remaining in the puncture opening throughout the remainder of the surgical procedure. Additionally, it is desirable that the seal device produce a small amount of resistance to the insertion force of surgical instruments passing through the trocar cannula. Furthermore, it is desirable that the sealing device maintain gas pressure in the abdominal cavity, despite numerous insertions and withdrawals of surgical instruments through the trocar cannula.

Current sealing devices for laparoscopic instruments are typified by particular valve designs such as that described in U.S. Pat. No. 5,224,952. This design includes a spring loaded valve in combination with a sealing gasket to conform to the cross section of the surgical instrument inserted through the trocar. This two part valve assembly performs adequately as a seal but may be more complex than truly desired. U.S. Pat. No. 5,141,498 shows at least three flexible leaflets, and U.S. Pat. No. 4,424,833 shows a sponge type valve with three connecting slits. Multiple leaflet and multiple slit valves may seal well when a surgical instrument is not inserted through them but will tend to create gaps around inserted instruments having circular cross sections and will also tend to cause eversion of their sealing surfaces when the instruments are withdrawn. Eversion of the sealing surfaces is likely to cause gaps between the sealing surfaces resulting in gas leakage through the seal. U.S. Pat. No. 5,242,412 shows a duck bill valve design applied to a trocar device. This design provides a straight single slit to seal against a surgical instrument. U.S. Pat. Nos. 4,475,548; 4,809,679; and 4,143,853 show single slit designs also. A single slit valve is also subject to a lack of conforming to circular shapes and to eversion upon withdrawal of surgical instruments.

Variations of the single slit design are shown in U.S. Pat. Nos. 4,798,594; 4,177,814; and 4,673,393. The variations shown in these patents encompass three slits radiating from the seal center and possess similar characteristics as the single slit regarding sealing around circular instruments and eversion. Other surgical valves include specialized designs typified by heart valves shown in U.S. Pat. Nos. 4,364,127; 3,861,416; and 4,222,126. These valves are designed to allow one direction flow of heavy liquids and include at least three flaps. Such valves are not intended to seal around surgical instruments against loss of gas pressure.

A study of these references indicates a need for a simpler one piece sealing valve assembly for use in trocars to seal against gas pressure during a laparoscopic surgical procedure. In addition, it is desirable to have a one piece assembly with a simple design which would not require an excessive force to insert an instrument through it and would resist eversion of the sealing edges once the surgical instrument is withdrawn.

SUMMARY OF THE INVENTION

According to the present invention, the object of providing and maintaining gas pressure during any laparoscopic surgical procedure is achieved using a one piece valve in a trocar device. One aspect of the invention comprises a self sealing flexible elastomeric valve having a flange with an aperture and a cylindrical wall extending from the flange. The sealing surface is provided by a pair of mutually opposed sealing wall sections extending from the cylindrical wall and converging at the distal end of the valve. At the distal end of the sealing wall sections, the opposed sealing wall sections are adjacent to each other and define a generally S-shaped slit. The S-shaped elastomeric sealing wall sections will conform to surgical instruments as they are inserted through the valve to seal against loss of gas pressure in the abdominal cavity. The self sealing flexible valve is preferably made from silicone rubber.

In another aspect of the invention, a trocar assembly is described incorporating the sealing valve described above. This assembly comprises a handle housing having a cannula passage, a cannula attached to the handle housing for receiving an obturator therethrough, a sealing valve as already described for self sealing when an obturator or other surgical instrument is inserted through, or withdrawn from the cannula, an obturator slidably received in the handle housing for insertion through the cannula, and an obturator handle attached to the obturator.

The elastomeric valve of this invention has the advantages of simplicity of manufacture and assembly, and the ability to provide an adequate seal against the surface of any surgical instrument inserted through it.

Also, this valve will require only a small amount of force to insert instruments, and will resist eversion of the valve walls when instruments are withdrawn. Once an instrument is withdrawn, the valve will still provide a seal.

The self sealing flexible elastomeric valve of this invention is used to effectively seal surgical instruments such as trocars against loss of gas pressure when surgical instruments are inserted during laparoscopic procedures. Additionally, the valve can be used to provide an effective seal when any other instruments or devices are inserted through it for any reason.

BRIEF DESCRIPTION OF THE DRAWINGS

FIG. 1 is a perspective view of the preferred valve of this invention as seen from the distal end.

FIG. 2 is a perspective view of the valve as seen from the proximal end.

FIG. 3 is a front elevational view of the valve.

FIG. 4 is a side elevational view of the valve.

FIG. 5 is a cross-sectional view of the valve.

FIG. 6 is a perspective view of a housing for a trocar handle and its attached cannula, where the preferred sealing valve is retained within the housing to provide a seal.

FIG. 7 is an exploded perspective view of a trocar assembly with the valve retained within the housing of the trocar handle.

FIG. 8 is an assembled perspective view of the trocar assembly with the valve in place.

FIG. 9 is a cross-sectional view of the trocar housing assembly with the valve in place.

DETAILED DESCRIPTION OF THE PREFERRED EMBODIMENT

Figure 10:
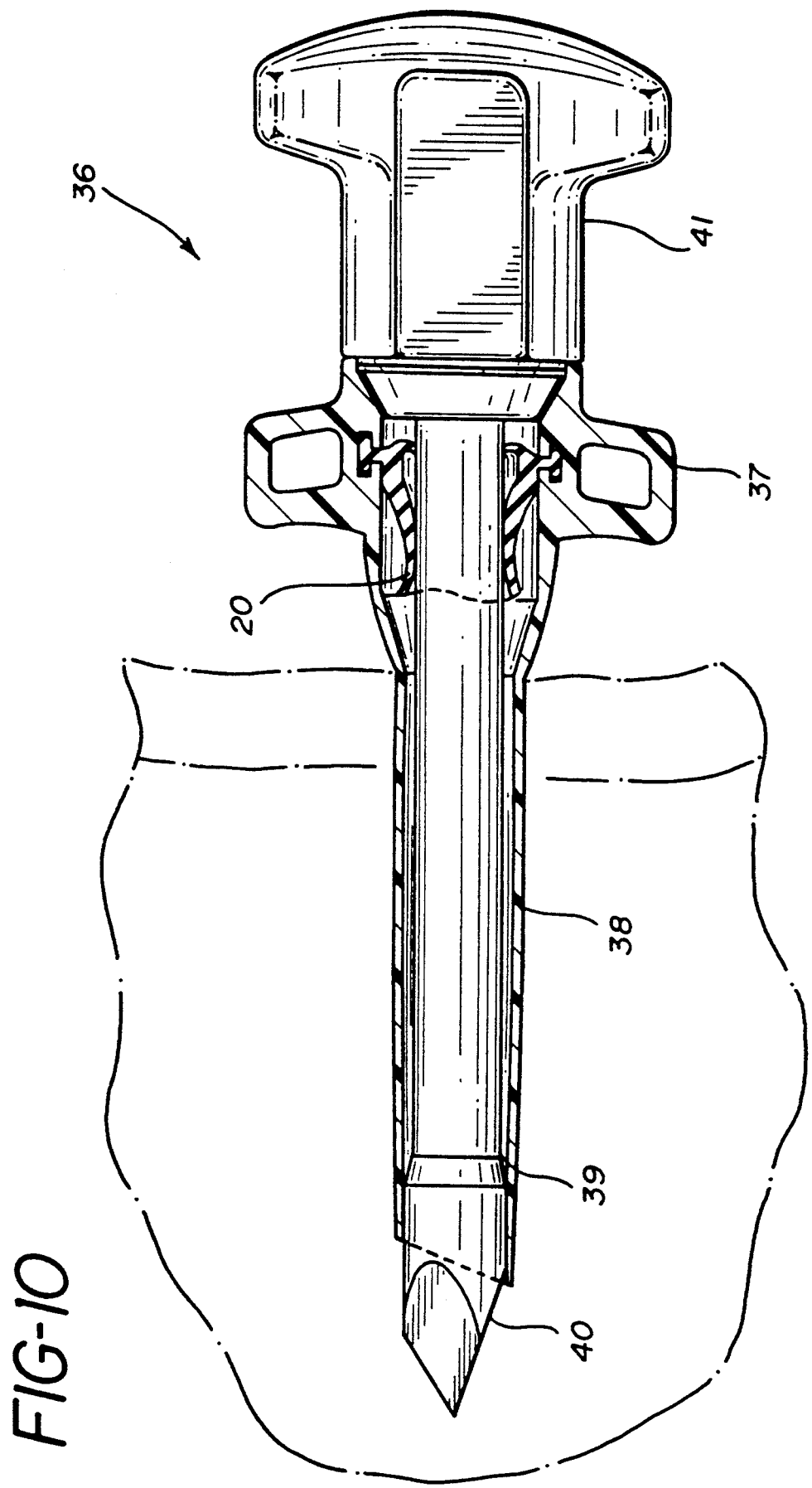
FIG. 10 is a partial cross section of the trocar assembly with the valve in place.

The self sealing flexible elastomeric valve and trocar assembly in which the valve is used are illustrated in FIGS. 1–12. The self sealing valve itself is shown in FIGS. 1–5 and its position and function in a trocar are shown in FIGS. 6–12.

Referring now to FIGS. 1 and 2, there are shown two views of a self sealing, one-piece valve 20. FIG. 1 shows a perspective view of valve 20 from its distal end and FIG. 2 shows the perspective view from its proximal end. The self sealing valve has a circular flange 21 with a concentrically located dome shaped region 32. Bordering the flange is a peripheral annular lip 30. The dome shaped region 32 has an aperture 22 which is concentric about the valve axis 33. The aperture 22 will expand because of the elastomeric nature of the valve when the trocar obturator or other surgical instrument is inserted through it. Therefore, continuous contact between the obturator or other instrument and the circumferential surface defining the aperture will result. This contact between the valve aperture and the surgical instrument provides sealing against loss of gas pressure from the body cavity. The valve axis 33 is shown on FIG. 4 and a cross section view through axis 33 is shown in FIG. 5. FIG. 4 also shows the flange plane 34 which is perpendicular to axis 33.

A cylindrical wall section 23 extends perpendicularly from flange 21 and defines a tubular opening 24. Extending from the cylindrical wall section 23 are a pair of generally frusto-conical shaped sealing walls 25, 26. These sealing walls are shown in FIGS. 1–5 but are more clearly shown in FIGS. 1, 3 and 5. The sealing walls 25, 26 extend from cylindrical wall section 23 and converge to become adjacent to each other at distal sealing ends 27, 28. The distal sealing ends are shaped in the form of an S-shaped slit 29. The surface of the slit is defined by a slit plane 35, which is parallel to flange plane 34 as shown in FIG. 4. Also, it can be seen at FIG. 4 that the slit 29 and flange aperture 22 lie on the longitudinal valve axis 33, perpendicular to the flange plane 34 and slit plane 35. The distal sealing ends 27, 28 form a gas pressure seal when no instrument is inserted through the valve. The walls also stretch to contact the surface of an inserted instrument to provide a seal around the instrument.

The valve 20 is composed of an elastomeric material. These materials include polymers having the elastic properties of natural rubber such as urethane polymers, vinyl polymers and silicone rubber. The most preferred material of construction is silicone rubber. Preferably, the wall thickness of the cylindrical wall section 23 of the valve is greater than either of the sealing wall sections 25, 26. This difference in thickness is preferred because the sealing walls 25, 26 must be more flexible than the cylindrical wall section 23 so that the sealing walls can snugly stretch to contact the surface of an inserted instrument. In this way, an acceptable seal can be achieved.

The self sealing elastomeric valve 20 is the sealing component of a trocar assembly 36 shown in FIGS. 6, 7, 8, and 10. FIG. 7 shows the major components of a typical trocar assembly and FIGS. 8 and 10 show the assembled trocar. The typical components include: a handle housing 37, a cannula 38 attached to the handle housing 37, an obturator 40, and an attached obturator handle 41. The cannula 38 and handle housing 37 contain a cannula passage 39 for receiving the obturator 40 or other surgical instrument.

Figure 11:
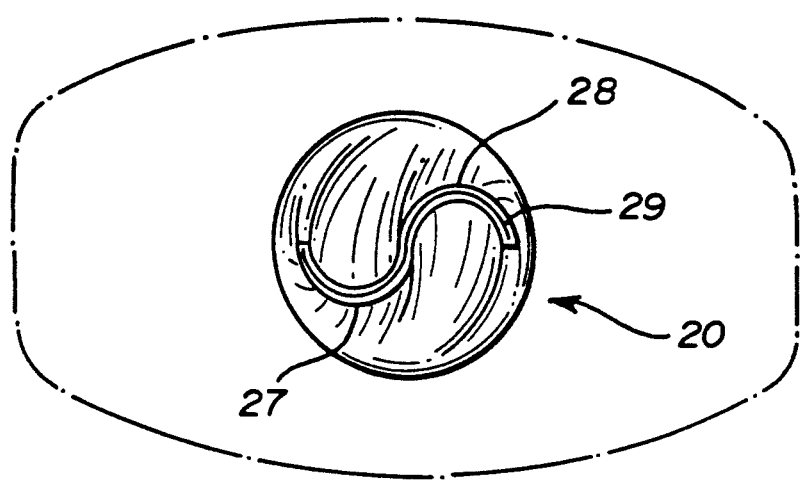
FIG. 11 is a schematic view of the preferred valve of the invention as seen from the distal end of the trocar cannula before the trocar obturator or other surgical instrument is inserted through the valve.
Figure 12:
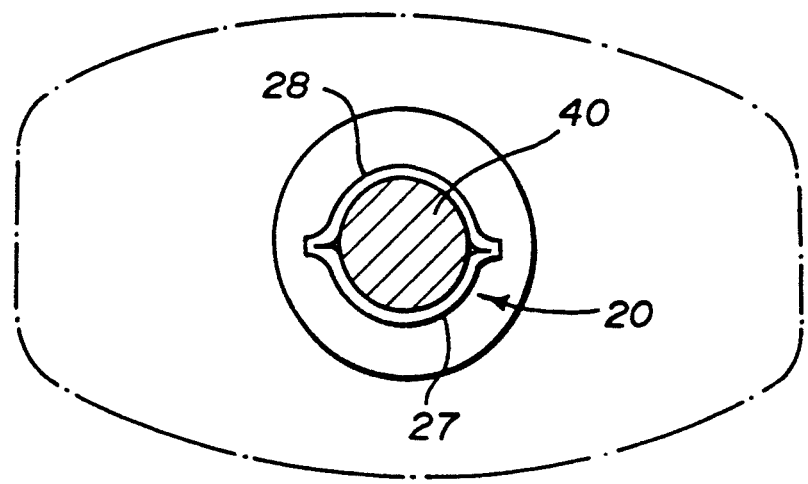
FIG. 12 is a schematic view of the valve as seen from the distal end of the trocar cannula as the obturator or other surgical instrument is inserted through the valve.

The valve 20 is restrained in the trocar handle housing 37 by a friction fit on lip 30 as shown in FIG. 9. FIG. 9 also shows the valve as a seal against loss of gas pressure with no instrument inserted. When a trocar obturator 40 or other surgical instrument is inserted, the valve 20 also seals against gas pressure loss as shown in FIGS. 10 and 12. In FIG. 10, the valve 20 is shown in a sectional view with the distal sealing ends 27, 28 of the sealing walls of the valve opened by an inserted obturator 40. A distal end view of the S-slit 29 with an obturator 40 inserted is shown in FIG. 12. The distal sealing ends 27, 28 conform to the shape of the instrument 40 inserted through them to cause a seal. FIG. 11 shows the same distal end view of the valve 20 with no instrument inserted. The sealing effect in this case is caused by both distal sealing ends 27, 28 remaining adjacent to each other in their undeformed state. Furthermore, the valve will always revert to this undeformed state when the obturator or other instrument is removed, thus continuously maintaining the necessary seal.

This invention has been described with respect to its most preferred embodiment. However, the reader should realize that numerous additional embodiments are contemplated within the scope of this invention as it is defined by the appended claims.

What is claimed is:

1. A self sealing flexible elastomeric valve adapted to have a device inserted therethrough, said valve comprising:
   a) a flange having an aperture therethrough,
   b) a cylindrical wall defining a tubular opening extending from said flange, and
   c) a pair of mutually opposed first and second sealing wall sections extending from said cylindrical wall, said first and second sealing wall sections each having a distal sealing end, said wall sections converging at said distal sealing ends wherein said wall sections are adjacent to each other and define a generally S-shaped slit.

2. The valve of claim 1 wherein said valve is a one-piece valve.

3. The valve of claim 2 wherein said cylindrical wall extends substantially perpendicularly from said flange.

4. The valve of claim 3 wherein said sealing wall sections converge in a manner wherein said valve has a generally frusto-conic shape.

5. The valve of claim 4 wherein said flange has a generally circular configuration and said aperture is centrally displayed on said flange.

6. The valve of claim 5 wherein said flange includes a peripheral annular lip.

7. The valve of claim 6 wherein said flange includes a concentrically dome shaped region.

8. The valve of claim 7 wherein said cylindrical wall has a thickness greater than the wall thickness of each of said first and second sealing wall sections.

9. The valve of claim 8 wherein said flange defines a flange plane, and said S-shaped slit defines a slit plane, and said slit plane is substantially parallel to said flange plane.

10. The valve of claim 9 wherein said flange aperture and said S-shaped slit define a longitudinal axis substantially perpendicular to said plane of said flange.

11. The valve of claim 1 wherein said flexible elastomeric valve is composed of a silicone rubber.

12. A trocar assembly comprising:
    a) a handle housing having a cannula passage,
    b) a cannula attached to said handle housing for receiving an obturator or other surgical instrument therethrough,
    c) the sealing valve of claim 1, said sealing valve retained in said housing for self sealing when said obturator or said other surgical instrument is inserted through said cannula or when said obturator or said other surgical instrument is withdrawn from said cannula,
    d) an obturator slidably received in said handle housing for insertion through said cannula, and
    e) an obturator handle attached to said obturator.

13. A trocar assembly comprising:
    a) a handle housing having a cannula passage,
    b) a cannula attached to said handle housing for receiving an obturator or other surgical instrument therethrough,
    c) the sealing valve of claim 10, said sealing valve retained in said housing for self sealing when said obturator or said other surgical instrument is inserted through said cannula or when said obturator or said other surgical instrument is withdrawn from said cannula,
    d) an obturator slidably received in said handle housing for insertion through said cannula, and
    e) an obturator handle attached to said obturator.

* * * * *